United States Patent [19]
de La Poterie et al.

[11] Patent Number: 5,843,412
[45] Date of Patent: Dec. 1, 1998

[54] QUICK-DRYING COLORED OR CLEAR NAIL VARNISH

[75] Inventors: Valérie de La Poterie, Le Chatelet en Brie; Myriam Mellul, L'Hay les Roses, both of France

[73] Assignee: L'Oreal, Paris, France

[21] Appl. No.: 676,407

[22] Filed: Jul. 8, 1996

Related U.S. Application Data

[63] Continuation of Ser. No. 302,877, filed as PCT/FR94/00086 Jan. 25, 1994, abandoned.

[30] Foreign Application Priority Data

Jan. 25, 1993 [FR] France .................................. 93 00692

[51] Int. Cl.$^6$ .............................. A61K 7/04; A61K 7/043
[52] U.S. Cl. ........................................... 424/61; 424/78.03
[58] Field of Search ................... 424/61, 78.03, 424/401

[56] References Cited

U.S. PATENT DOCUMENTS

| | | | |
|---|---|---|---|
| 3,893,984 | 7/1975 | Hager et al. | 260/79.7 |
| 3,952,066 | 4/1976 | Glickman et al. | 252/8.9 |
| 4,166,110 | 8/1979 | Isobe et al. | |
| 4,563,347 | 1/1986 | Starch | 424/70.122 |
| 4,749,732 | 6/1988 | Kohl | 524/43 |
| 4,873,077 | 10/1989 | Thompson et al. | 424/61 |
| 5,045,309 | 9/1991 | Dell'Aquila | 424/61 |
| 5,118,496 | 6/1992 | Herstein | 424/63 |
| 5,160,733 | 11/1992 | Berthiaume | 424/70.122 |
| 5,176,906 | 1/1993 | Lamb et al. | 424/70.122 |
| 5,225,195 | 7/1993 | Sovama | 424/401 |
| 5,275,807 | 1/1994 | Pappas | 424/61 |
| 5,368,847 | 11/1994 | Brunetta | 424/61 |

FOREIGN PATENT DOCUMENTS

| | | |
|---|---|---|
| 1166696 | 1/1986 | European Pat. Off. . |
| 0295780 | 12/1988 | European Pat. Off. . |
| 0370470 | 5/1990 | European Pat. Off. . |
| 0432572 | 6/1991 | European Pat. Off. . |
| 0558423 | 9/1993 | European Pat. Off. . |
| 1356552 | 6/1964 | France . |
| 1378794 | 2/1965 | France . |
| 2379280 | 9/1978 | France . |
| 2397186 | 2/1979 | France . |
| 2478998 | 10/1981 | France . |
| 2499851 | 8/1982 | France . |
| 2611730 | 9/1988 | France . |
| 2617043 | 12/1988 | France . |
| 2679445 | 1/1993 | France . |
| 2684668 | 6/1993 | France . |
| 2052579 | 4/1972 | Germany . |
| 2702607 | 7/1977 | Germany . |
| 55-138316 | 10/1980 | Japan . |
| 59-199621 | 11/1984 | Japan . |
| 63-2916 | 1/1988 | Japan . |
| 63-183508 | 7/1988 | Japan . |
| 1-193236 | 8/1989 | Japan . |
| 4-275268 | 9/1992 | Japan . |
| 1182939 | 3/1970 | United Kingdom . |
| 1199776 | 7/1970 | United Kingdom . |

*Primary Examiner*—Sally Gardner-Lane
*Attorney, Agent, or Firm*—Oliff & Berridge, PLC

[57] ABSTRACT

A colored or colorless nail varnish containing, in a varnish solvent system, a film-forming substance, a resin and a plasticizer as well as a combination of (i) 0.05–5 wt % an amino or thio silicone and (ii) 0.05–5 wt % of an organofluorinated hydrocarbon compound, the total weight of (i)+(ii) being at most 5 wt % of the total weight of the varnish. The varnishes have an improved drying time.

15 Claims, No Drawings

QUICK-DRYING COLORED OR CLEAR NAIL VARNISH

This is a Continuation of application Ser. No. 08/302,877 filed Oct. 28, 1994, now abandoned.

FIELD OF THE INVENTION

The subject of the present invention is a coloured or clear nail varnish containing, in addition to the usual ingredients, a combination of an amino- or thiosilicone and an organofluorinated hydrocarbon compound.

Mention must very particularly be made, among the main characteristics which nail varnishes must possess, of the absence of skin and nail irritation and the production of a film which is homogeneous and has a good gloss but which also has good adhesion to the surface of the nail as well as possessing a certain flexibility and strength, this with a view to avoiding brittleness thereof which can result in cracking of the varnish.

BACKGROUND

Generally, use is currently made, to confer good adhesion, of plasticizers and modified resins, which results in the varnish possessing good flexibility.

With a view to improving adhesion, the application of a coupling prelayer or alternatively the introduction of certain additives making it possible to improve adhesion has also been proposed.

The use of silicone in nail varnishes as additive has already been described with the aim of improving the resistance to water and of facilitating spreading of the varnish.

Thus, in U.S. Pat. No. 4,873,077, the use of a fluid silicone with a view to improving the smoothness of the film after evaporation of the solvent and of improving its resistance to moisture was proposed.

Likewise, in JP-A-55.139316 and 59.199621, the use of silicones, in particular of methyl- or dimethylpolysiloxane, for improving the gloss and the resistance to water and to abrasion of the varnish film was also proposed.

Nail varnish compositions forming films easily detachable from the nails without the aid of varnish remover have been described in FR 78.02721 (2,379,280).

According to this patent, the varnish composition contains, in addition to the usual ingredients, from 0.01 to 30 parts by weight, with respect to the natural or synthetic resin, of an organopolysiloxane carrying various functional groups, optionally including amine functional groups. The presence of organopolysiloxane is essential with a view to obtaining a film which is easily detachable or peelable from the surface of the nail.

The use of organofluorinated compounds in nail varnishes and more particularly of fluorocarbon resins had been recommended in EP 370,470 only as fluorescent pigment binder.

SUMMARY OF THE INVENTION

After much research, it has now been found, entirely surprisingly and unexpectedly, that it was possible, by using in a nail varnish composition a certain, very specific, class of organopolysiloxanes containing amine or thiol functional group(s), hereinafter denoted by the expressions "aminosilicones" and "thiosilicones", in combination with an organofluorinated hydrocarbon compound, to particularly significantly improve the drying time of coloured or clear varnishes on nails as well as, most often, their adhesion.

The subject of the present invention is therefore, as novel industrial product, a coloured or clear nail varnish containing, in a varnish solvent system, a film-forming substance, a resin and a plasticizer, the said varnish additionally containing, with a view to improving the drying time, the combination of (i) 0.05 to 5 weight % of an amino- or thiosilicone and (ii) 0.05 to 5 weight % of an organofluorinated hydrocarbon compound, the total weight of (i)+(ii) having to be less than or equal to 5 weight % of the total weight of the varnish.

DESCRIPTION OF PREFERRED EMBODIMENTS

The aminosilicones of the varnish according to the invention can be represented by the following general formula:

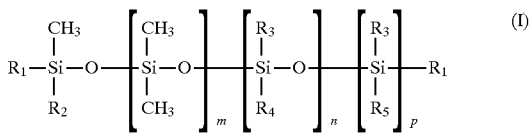

wherein $R_1$ represents $CH_3$, $OCH_3$, $OCH_2CH_3$ or $-(CH_2)_d-NH_2$ $R_2$ represents $CH_3$, $OCH_3$ or $OCH_2CH_3$, $R_3$ represents $CH_3$, $OCH_3$, $OCH_2CH_3$ or $OSi(CH_3)_3$, $R_4$ represents $CH_3$ or

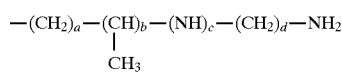

$R_5$ represents $CH_3$, $OCH_3$, $OCH_2CH_3$ or

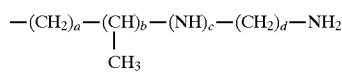

a is 0 to 6 b is 0 to 2 c is 0 or 1 d is 1 to 6 with the proviso that:
(i) when $R_1$ represents the $-(CH_2)_d-NH_2$ radical, $R_4$ represents $CH_3$ and $R_5$ represents $CH_3$, $OCH_3$ or $OCH_2CH_3$,
(ii) when $R_4$ represents $CH_3$, $R_5$ represents:

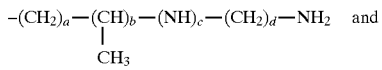 and (iii) when $R_4$ represents

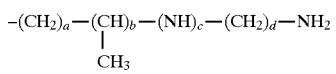

$R_5$ represents $CH_3$, $OCH_3$ or $OCH_2CH_3$, m is 1 to 1,000 n is 0 to 50 and p is 0 to 50 it not being possible for n and p to simultaneously be 0, the molecular weight of the said aminosilicone being between 500 and 100,000.

The aminosilicone must preferably have an amine index (meq/g) of between 0.05 and 2.3 and preferably 0.05 and 0.50.

The molecular weight of the aminosilicone of formula (I) is preferably between 1,000 and 20,000.

Mention may especially be made, among aminosilicones of formula (I), of those sold by the Company Shin-Etsu under the names "KF860", "KF861", "KF862", "KF864", "KF865", "KF867", "X22-3680" and "X22-3801C", those sold by the Company Wacker under the names "SLM 55051", "L656", "SLM 55067", "VP1653" and "VP1480M", that sold by the Company Dow Corning under the name of "DC929", those sold by the Company Goldschmidt under the names of "Tegomer A-Si2320" or "Tegomer A-Si2120", and that sold by the Company General Electric under the name of "SF 1706".

The aminosilicones can be provided in the form of a pure oil or in the form of an aqueous emulsion containing from 5 to 50% of active material, such as the product "QS-7224" sold by the Company Dow Corning or the product "SLM 23047" sold by the Company Wacker.

The thiosilicones of the varnishes according to the invention are polydiorganosiloxanes containing, in their molecule, at least one unit of formula:

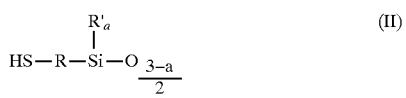

in which:

R denotes a divalent aliphatic radical having from 2 to 26 carbon atoms which is optionally interrupted by an ester functional group and which can carry ethylene oxide or propylene oxide units or their mixture, R' denotes a monovalent hydrocarbon radical having 1 to 6 carbon atoms, an alkoxy radical having 1 to 4 carbon atoms or a trimethylsilyloxy radical, a is equal to 0, 1 or 2, the remaining units having the formula:

in which:

R" represents a $C_1$–$C_{18}$ alkyl, phenyl($C_1$–$C_6$)alkyl or phenyl group, b is equal to 1, 2 or 3, at least 50% of the R' and R" groups representing a methyl group, and 2) optionally units of formula:

in which

R" is as defined above and n is an integer from 1 to 18.

The degree by weight of the thiol groups present in the polydiorganosiloxane is preferably between 0.1 and 15% and in particular between 0.15 and 13%.

According to a specific embodiment, the R radical represents a group —$(CH_2)_n$—, where n is between 3 and 8, or a group of formula:

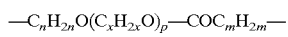

in which:

n represents an integer between 1 and 18, m represents an integer between 1 and 8, x=2 or 3 and when x=3, the $C_3H_6$ radical is branched and p is equal to 0 or denotes a number which can range up to 40, and R' represents a $C_1$–$C_6$ alkyl radical such as methyl, ethyl, n-propyl, isopropyl or n-butyl.

The R" radical preferably represents a methyl group and the R radical preferably represents —$(CH_2)_2$—, —$(CH_2)_3$— or —$(CH_2)_4$—.

The total number of the units of formula (II), (III) and optionally (IV) is preferably equal to or less than 500 and in particular between 10 and 500.

Such thiosilicones are especially described in GB-1,182,939, GB-1,199,776, FR-1,356,552 and 1,378,791, and EP-A-295,780 and FR-A-2,611,730.

Mention may be made, among thiosilicones as defined above, of those sold by the Company Wacker under the names of "VP1641" or "SLM 50253/6", those sold by the Company Shin-Etsu under the names of "X22-980" and "X22-167B" and those sold by the Company Genesee under the names of "GP72-A" and "GP71".

The organofluorinated hydrocarbon compound of the varnish according to the invention is non-volatile, its boiling point being greater than 30° C.

Such organofluorinated hydrocarbon compounds have a chemical structure containing a carbon skeleton where certain hydrogen atoms have been substituted by fluorine atoms, it being possible for the carbon skeleton to contain one or a number of hetero atoms and one or a number of functional organic groups.

For organofluorinated hydrocarbon compounds, the degree of substitution of hydrogen atoms by fluorine atoms is defined in the form of the ratio: number of fluorine atoms/(number of fluorine atoms+number of hydrogen atoms), where only the hydrogen atoms bonded to the carbon atoms of the skeleton are taken into account.

The organofluorinated hydrocarbon compounds as defined above can be represented by the following general formula:

in which:

x represents 1, 2 or 3, y represents 0 or 1, z represents 0, 1, 2 or 3, with the condition that y and z are not simultaneously 0 and that when z is 0, x is 2 or 3.

$R_F$ represents a saturated or unsaturated, aliphatic or aromatic fluorinated radical containing a linear, branched or cyclic chain, it being possible for this chain to be functionalized and/or be interrupted by divalent atoms such as oxygen or sulphur or trivalent atoms such as nitrogen and/or substituted by hydrogen atoms or other halogen atoms, with the condition that not more than one of these substituents, other than fluorine, is present per two carbon atoms of the skeleton, $R_H$ represents a saturated or unsaturated, aliphatic or aromatic hydrocarbon radical containing a linear, branched or cyclic chain, it being possible for this chain to be functionalized and/or interrupted by one or a number of divalent atoms such as oxygen or sulphur or by one or a number of trivalent atoms such as nitrogen, A represents a di-, tri- or tetravalent radical such as $$O-\overset{\overset{O}{\|}}{\underset{|}{P}}-O,$$
$$\phantom{O-}O$$

aliphatic or aromatic cyclic structures or ethylenic unsaturations.

The expression "functionalized" is understood to mean, according to the invention, an end or pendent substitution of the inserted skeleton by at least one organic functional group such as an alcohol, thiol, acid, carbonyl, sulphoxide, ester, amide, amine, phosphate, ethylenic, acetylenic and enamine or sulphonamide functional group.

Ethylenic unsaturation is understood to mean, for example, $$\diagdown C=C\diagup \quad , \quad \diagdown C=CH- \quad \text{or} \quad -CH=CH-$$

$R_H$ preferably represents a linear or branched $C_1$–$C_{22}$ alkyl radical or a mixture of linear or branched $C_1$–$C_{22}$ alkyl radicals, a $C_6$–$C_{10}$ aryl radical or a $C_7$–$C_{15}$ aralkyl radical.

$R_F$ preferably represents a perfluoroalkyl radical having from 4 to 22 carbon atoms.

According to the invention, the organofluorinated hydrocarbon compounds used preferably have a degree of substitution of between 0.5 and 95% but preferably greater than 10% and less than 80%.

Mention may be made, by way of illustration, of compounds possessing perfluorocarbon groups and hydrocarbon groups, the total carbon number being between 10 and 30 and the number of carbon atoms of the hydrocarbon groups being equal to or greater than twice the number of carbon atoms of the perfluorocarbon groups, such compounds being described in JP-A-63.002916.

Mention may likewise be made, by way of illustration, of organofluorinated hydrocarbon compounds whose general structure is defined by the following formula (VI):

$$R_1-(CH_2)_n-X-[C_3H_5(OH)]-(Y)_x-(CH_2)_m-R_2 \quad (VI)$$

in which:
the divalent radical $C_3H_5(OH)$ represents at least one of the following divalent radicals:

$$-CH_2-\underset{\underset{OH}{|}}{CH}-CH_2-, \quad (a)$$

$$-\underset{\underset{CH_2OH}{|}}{CH}-CH_2- \quad \text{and} \quad (b)$$

$$-CH_2-\underset{\underset{CH_2OH}{|}}{CH}- \quad (c)$$

$R_1$ represents a linear or branched $C_4$–$C_{20}$ perfluoroalkyl radical or a mixture of such linear or branched $C_4$–$C_{20}$ perfluoroalkyl radicals, $R_2$ represents $R_1$ or a linear or branched $C_1$–$C_{22}$ alkyl radical or a mixture of such linear or branched $C_1$–$C_{22}$ alkyl radicals or a $C_6$–$C_{10}$ aryl or $C_7$–$C_{15}$ aralkyl radical, with the proviso that:
(i) when $R_2$ is different from $R_1$, X and Y represent —O—, —S—, $$\underset{-S-}{\overset{\overset{O}{\uparrow}}{\phantom{|}}} \quad \text{or} \quad \underset{-S-}{\overset{O\diagdown\!\!\diagup O}{\phantom{|}}}$$

it not being possible for X and Y simultaneously to represent $$\underset{-S-}{\overset{\overset{O}{\uparrow}}{\phantom{|}}} \quad \text{or} \quad \underset{-S-}{\overset{O\diagdown\!\!\diagup O}{\phantom{|}}},$$

and (ii) when $R_2$ represents $R_1$, X and Y, which are identical, represent —O— or —S— m and n, which are identical or different, are between 0 and 4 and x represents 0 or 1.

The compounds of formula (VI) above are more particularly described in FR 91/15019, EP-A-166,696, DE 2,702,607, JP 89/193,236, JP 92/275,268 and U.S. Pat. No. 3,893,984.

Mention may be made, as examples of compounds of formula (VI), of:

1-(2'-(F-hexyl)ethylthio)-3-(2"-ethylhexyloxy)-2-propanol, 1-(2'-(F-octyl)ethylthio)-3-(2"-ethylhexyloxy)-2-propanol, 1-(2'-(F-octyl)ethylthio)-3-butyloxy-2-propanol, 1-(2'-(F-octyl)ethylthio)-3-phenoxy-2-propanol, 1-(2'-(F-hexyl)ethylthio)-3-dodecyloxy-2-propanol, 1-(2'-(F-hexyl)ethylthio)-2-decanol, 1-(2'-(F-hexyl)ethylthio)-2-hexanol, 1-(2'-(F-octyl)ethylthio)-2-hexanol, 1-(2'-(F-hexyl)ethyloxy)-3-(2"-ethylhexyloxy)-2-propanol, 1-(2'-(F-hexyl)ethylthio)-3-octylthio-2-propanol, 1-(2'-(F-octyl)ethylthio)-3-octadecylthio-2-propanol, 1,3-bis(2'-(F-hexyl)ethylthio)-2-propanol, and 1,3-bis(2'-(F-octyl)ethylthio)-2-propanol.

Mention may also be made, as other organofluorinated hydrocarbon compounds, of those corresponding to the following formulae (X) and (XI):

$$R_1-CH_2-CH_2-X-CH_2-\underset{\underset{Y}{|}}{CH}-Z \quad (X)$$

in which:

$R_1$ represents a linear or branched $C_4$–$C_{20}$ perfluoroalkyl radical or a mixture of such linear or branched $C_4$–$C_{20}$ perfluoroalkyl radicals, Y is either (i) OH and Z represents —$CH_3$, —$CH_2OH$, —$CH_2OCOCH_3$ or —$C_6H_5$, or (ii) —$CH_2OH$ and Z represents —$OCOCH_3$, and X represents —O—, —S—

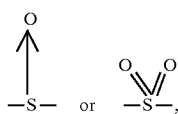

 (XI)

in which:

the divalent radical $C_3H_5(OH)$ represents at least one of the following divalent radicals:

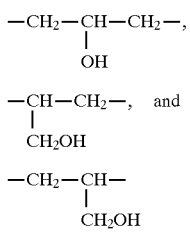

$R_1$ represents a linear or branched $C_4$–$C_{20}$ perfluoroalkyl radical or a mixture of such linear or branched $C_4$–$C_{20}$ perfluoroalkyl radicals, W represents —OR, —SR, —COOR, —O—$C_6H_5$, o- or p-O—$C_6H_4$ ($CH_3$) or o- or p-O—$C_6H_4$(OH), R representing a linear or branched $C_1$–$C_{18}$ alkyl radical.

The compounds of formula (X) are more particularly described in DE 2,052,579 and those of formula (XI) in U.S. Pat. No. 3,952,066.

Mention may especially be made, among the latter, of:

2-(2'-(F-hexyl)ethylthio)-1-phenylethanol, 2-(2'-(F-hexyl)ethylsulphonyl)-1-phenylethanol, 1-(3'-(F-hexyl)-2'-propenoxy)-3-octylthio-2-propanol, 1-(3'-(F-hexyl)-2'-propenoxy)-3-butyloxy-2-propanol, and 1-(3'-(F-octyl)-2'-propenoxy)-3-octadecylthio-2-propanol.

Additionally, it is possible to use, according to the invention, as organofluorinated hydrocarbon compounds, those sold under the name of "Nofable Fo" by the Company Nippon Oil & Co., having the following formula:

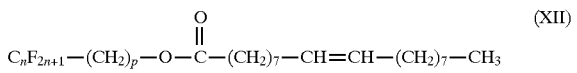 (XII)

in which:

n is an integer equal to 6 or 8 and p is 1 or 2.

Finally, mention may also be made of the organofluorinated compounds corresponding to the following formula (XIII):

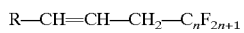 (XIII)

in which:

R denotes a butyl or phenyl radical and n is 4, 6 or 8.

Such compounds are described in B. Escoula, Synthetic Communications, 15(1), 35–38 (1985).

The organofluorinated hydrocarbon compounds used according to the invention are preferably provided in the oil or wax form.

The combination of the amino- or thiosilicone and of the organofluorinated hydrocarbon compound makes it possible, as shown in the examples given hereinbelow, to reduce the drying time by at least approximately 50% and can cause a large increase in the adhesion of the varnish to the nails.

According to the invention, it is also possible to combine, with the varnish, a silicone gum or a silicone resin in a low percentage of the order of 0.1 to 2 weight % and preferably of 0.3 weight % in order to improve the spreading, the smooth appearance of the film and the gloss.

According to the invention, the solvent system of the varnish is generally present in a proportion of between 55 and 90 weight % with respect to the total weight of the varnish.

This solvent system essentially consists of a mixture of various volatile organic solvents, with a view to obtaining relatively short drying times.

Mention may be made, among these solvents, of acetone, ethyl acetate, butyl acetate, 2-methoxyethyl acetate, methyl ethyl ketone, methyl isobutyl ketone, methyl acetate, amyl acetate and isopropyl acetate.

The solvent system can also comprise a diluent, which is preferably a linear or branched saturated hydrocarbon such as hexane or octane or alternatively an aromatic hydrocarbon such as toluene or xylene in a proportion generally of between 10 and 35% with respect to the total weight of the varnish.

The solvent system can also include other volatile solvents such as ethanol, n-butanol, n-propanol, isopropanol or their mixtures.

The film-forming substance is generally present in the varnish according to the invention at a concentration of between 5 and 20 weight % and preferably between 10 and 20 weight % with respect to the total weight of the varnish.

Mention may be made, among preferred film-forming substances, of nitrocelluloses of "RS" or "SS" type and in particular RS ¼ second nitrocellulose, RS ½ second nitrocellulose, SS ½ second nitrocellulose and RS ¾ second nitrocellulose.

It is also possible to use according to the invention, as secondary film-forming substance, polyvinyl derivatives such as poly(vinyl butyrate) as well as the copolymers described in FR 80.07328, 81.03199 and 88.08172.

According to the invention, the plasticizer is generally present in the varnish at a concentration of between 2 and 10 weight % with respect to the total weight of the varnish.

The plasticizers make it possible to adjust the flexibility of the film without weakening its resistance or its physical strength. Mention may be made, among plasticizers capable of being used in the varnishes according to the invention, of: tricresyl phosphate, benzyl benzoate, tributyl phosphate, butyl acetylricinoleate, glyceryl acetylricinoleate, dibutylphthalate, butyl glycolate, dioctyl phthalate, butylstearate, tributoxyethyl phosphate, triphenyl phosphate, triethyl citrate, tributyl citrate, tributyl acetylcitrate, tri(2-ethylhexyl) acetylcitrate, dibutyl tartrate, dimethoxyethyl phthalate, diisobutyl phthalate, diamyl phthalate, camphor, glycerol triacetate and their mixtures.

According to the invention, the nail varnish also contains a resin generally present in a proportion of between 0.5 and 15 weight % with respect to the total weight of the varnish.

Among the many resins which can be used, it is preferable to employ according to the invention resins of the arylsulphonamide-formaldehyde or arylsulphonamide-epoxy type, especially the toluenesulphonamide-formaldehyde resin most known under the tradenames of "Santolite MHP", "Santolite MS 80%" and "Ketjenflex MS80" or alternatively alkyd resins such as those sold by the Company Dainippon under the name of "Beckosol ODE 230-70".

These resins, while increasing the film-forming power, improve the gloss and the adhesion.

When the nail varnish according to the invention is a coloured varnish, then at least one pigment of organic or inorganic nature is used.

Mention may be made, among organic pigments, of D & C Red No. 10, 11, 12 and 13, D & C Red No. 7, D & C Red No. 5 and 6, D & C Red No. 34, and lakes such as D & C Yellow No. 5 Lake and D & C Red No. 2 Lake.

Mention may be made, among inorganic pigments, of titanium dioxide, bismuth oxychloride, brown iron oxide and red iron oxides. Mention may be made, as organic pigment, of guanine.

According to this embodiment, the pigments are generally present in a proportion between 0.01 and 2 weight % with respect to the total weight of the varnish.

Finally, in order to avoid sedimentation of the pigments, certain thixotropic agents can be employed, such as, for example, "Bentone 27" or "Bentone 38".

The nail varnishes according to the invention can additionally contain adjuvants commonly used in nail varnishes. Mention may be made, among these adjuvants, of U.V. screening agents such as benzophenone derivatives and ethyl 2-cyano-3,3-diphenylacrylate.

A number of examples of nail varnishes according to the invention will now be given by way of illustration.

PREPARATION EXAMPLES

Example 1

1-(2'-(F-hexyl)ethylthio)-3-(2"-ethylhexyloxy)-2-propanol 3.6 g of a methanolic solution of sodium methoxide (approximately 30%–5.54 meq.g$^{-1}$) are added over one minute, at a temperature of 25° C., with stirring and. under a stream of nitrogen, to 152 g of 2-(F-hexyl)-ethanethiol.

The mixture is heated to 70° C. and then the methanol present in the mixture is evaporated under vacuum.

2-Ethylhexyl glycidyl ether (74.4 g) is then added dropwise over one hour. The temperature of the mixture is maintained between 60° and 70° C. during the addition of the epoxide.

At the end of the addition, the temperature is brought to 25° C. and the mixture is neutralized using 20 ml of normal HCl and the 1-(2'-(F-hexyl)ethylthio)-3-(2"-ethylhexyloxy)-2-propanol is separated by distillation: B.p.=141° C./66.5 Pa.

175 g (77%) of a colourless translucent oil are obtained.

| | Elemental analysis: | | | |
|---|---|---|---|---|
| | C % | H % | S % | F % |
| Calculated | 40.28 | 4.80 | 5.66 | 43.60 |
| Found | 40.37 | 4.82 | 5.55 | 43.74 |

Example 2

1-(2'-(F-octyl)ethylthio)-3-phenoxy-2-propanol 2.65 g of a methanolic solution of sodium methoxide (5.65 meq.g$^{-1}$) are added, at a temperature of 25° C., with stirring and under a stream of nitrogen, to 144 g (0.3 mol) of 2-(F-octyl)ethanethiol in solution in 250 ml of diisopropyl ether.

The mixture is heated while maintaining the temperature between 55° and 65° C. and 45 g (0.3 mol) of phenyl glycidyl ether are added dropwise over 45 minutes.

At the end of the reaction, the mixture is neutralized with 15 ml of normal HCl.

After evaporation of the solvent, a pasty product is obtained which is pale-yellow in colour.

The 1-(2'-(F-octyl)ethylthio)-3-phenoxy-2-propanol is purified by distillation (166°–168° C./13.3 Pa).

115 g of a white solid are obtained after cooling and crystallization.

Yield: 65%

Melting point: 64° C.

| | Elemental analysis: | | | |
|---|---|---|---|---|
| | C % | H % | S % | F % |
| Calculated | 36.20 | 2.40 | 5.09 | 51.24 |
| Found | 36.20 | 2.38 | 4.94 | 51.19 |

Examples of Nail Varnishes

| EXAMPLE 1 | |
|---|---|
| Nitrocellulose | 10.84% |
| Toluenesulphonamide-formaldehyde resin | 9.76% |
| Tributyl acetylcitrate | 6.51% |
| Toluene | 30.97% |
| Butyl acetate | 21.685% |
| Ethyl acetate | 9.29% |
| Isopropyl alcohol | 7.74% |
| Stearalkonium hectorite | 1.35% |
| Pigments | 1.00% |
| Citric acid | 0.055% |
| 1-(2'-(F-Hexyl)ethylthio)-3-(2"-ethyl-hexyloxy)-2-propanol | 0.5% |
| Aminosilicone "KF-865" of the-Company Shin-Etsu | 0.3% |

Drying time (30° C.–50% relative humidity)=15 minutes

| EXAMPLE 2: (comparative) | |
|---|---|
| Nitrocellulose | 10.93% |
| Toluenesulphonamide-formaldehyde resin | 9.85% |
| Tributyl acetylcitrate | 6.565% |
| Toluene | 31.22% |
| Butyl acetate | 21.86% |
| Ethyl acetate | 9.36% |
| Isopropyl alcohol | 7.80% |
| Stearalkonium hectorite | 1.36% |
| Pigments | 1.00% |
| Citric acid | 0.055% |

Drying time (30° C.–50% relative humidity)=27 minutes

The drying time of this varnish, which does not contain the combination of an aminosilicone and an organofluorinated hydrocarbon compound, is much longer than that of the varnish of Example 1.

Example 3 (comparative)

| EXAMPLE 3 (comparative) | |
| --- | --- |
| Nitrocellulose | 10.84% |
| Toluene sulphonamide-formaldehyde resin | 9.76% |
| Tributyl acetylcitrate | 6.51% |
| Toluene | 30.97% |
| Butyl acetate | 24.685% |
| Ethyl acetate | 9.29% |
| Isopropyl alcohol | 7.74% |
| Stearalkonium hectorite | 1.35% |
| Pigments | 1.00% |
| Citric acid | 0.055% |
| 1-(2'-(F-Hexyl)ethylthio)-3-(2"-ethyl-hexyloxy)-2-propanol | 0.5% |
| Phenyldimethicone "Belsil PDM 200" of the Company Wacker | 0.3% |

Drying time (30° C.–50% relative humidity)=22 minutes

This comparative example shows that the presence of a silicone of the type which does not carry functional amino (phenyldimethicone) does not make it possible to reduce the drying time.

| EXAMPLE 4: (comparative) | |
| --- | --- |
| Nitrocellulose | 10.9% |
| Toluene sulphonamide-formaldehyde resin | 9.8% |
| Tributyl acetylcitrate | 6.495% |
| Toluene | 31.105% |
| Butyl acetate | 21.8% |
| Ethyl acetate | 9.395% |
| Isopropyl alcohol | 7.8% |
| Stearalkonium hectorite | 1.35% |
| Pigments | 1.00% |
| Citric acid | 0.055% |
| Aminosilicone "KF 865" of the Company Shin-Etsu | 0.3% |

Drying time (30° C.–50% relative humidity)=18 minutes

This example, which does not contain organofluorinated hydrocarbon compound, makes it possible to show, with respect to Example 1, that the drying time is increased by more than 15%.

| EXAMPLE 5: (comparative) | |
| --- | --- |
| Nitrocellulose | 10.88% |
| Toluenesulphonamide-formaldehyde resin | 9.779% |
| Tributyl acetylcitrate | 6.481% |
| Toluene | 31.04% |
| Butyl acetate | 21.76% |
| Ethyl acetate | 9.375% |
| Isopropyl alcohol | 7.78% |
| Stearalkonium hectorite | 1.35% |
| Pigments | 1.00% |
| Citric acid | 0.055% |
| 1-(2'-(F-Hexyl)ethylthio)-3-(2"-ethyl-hexyloxy)-2-propanol | 0.5% |

Drying time (30° C.–50% relative humidity)=25 minutes

This example shows that the organofluorinated hydrocarbon compound alone has virtually no influence on the reduction in the drying time with respect to Example 2 (comparative).

| EXAMPLE 6 | |
| --- | --- |
| Nitrocellulose | 10.76% |
| Toluenesulphonamide-formaldehyde resin | 9.69% |
| Tributyl acetylcitrate | 6.455% |
| Toluene | 30.75% |
| Butyl acetate | 21.53% |
| Ethyl acetate | 9.23% |
| Isopropyl alcohol | 7.68% |
| Stearalkonium hectorite | 1.35% |
| Pigments | 1.00% |
| Citric acid | 0.055% |
| 1-(2'-(F-Hexyl)ethylthio)-3-phenoxy-2-propanol | 1.0% |
| Aminosilicone "KF 865" of the Company Shin-Etsu | 0.5% |

Drying time (30° C.–50% relative humidity)=12 minutes

| EXAMPLE 7 | |
| --- | --- |
| Nitrocellulose | 10.84% |
| Toluene sulphonamide-formaldehyde resin | 9.76% |
| Tributyl acetylcitrate | 6.51% |
| Toluene | 30.97% |
| Butyl acetate | 21.685% |
| Ethyl acetate | 9.29% |
| Isopropyl alcohol | 7.14% |
| Stearalkonium hectorite | 1.35% |
| Pigments | 1.00% |
| Citric acid | 0.055% |
| Aminosilicone "KF 865" of the Company Shin-Etsu | 0.5% |
| Organofluorinated hydrocarbon compound "Nofable Fo 9982" of the Company Nippon Oil | 0.3% |

Drying time (30° C.–50% relative humidity)=14.5 minutes

| EXAMPLE 8 | |
| --- | --- |
| Nitrocellulose | 10.84% |
| Toluenesulphonamide-formaldehyde resin | 9.76% |
| Tributyl acetylcitrate | 6.51% |
| Toluene | 30.97% |
| Butyl acetate | 21.685% |
| Ethyl acetate | 9.29% |
| Isopropyl alcohol | 7.74% |
| Stearalkonium hectorite | 1.35% |
| Pigments | 1.00% |
| Citric acid | 0.055% |
| Aminosilicone "KF 865" of the Company Shin-Etsu | 0.5% |
| 1-(2'-(F-Hexyl)ethylthio)-3-(2"-ethylhexyloxy)-2-propanol | 0.3% |

Drying time (30° C.–50% relative humidity)=13 minutes

A test carried out on a panel of 60 women with this varnish showed that the users had observed a very marked improvement in the drying time with respect to the same varnish but not containing the claimed combination.

| EXAMPLE 9 | |
| --- | --- |
| Nitrocellulose | 10.84% |
| Toluenesulphonamide-formaldehyde resin | 9.76% |
| Tributyl acetylcitrate | 6.51% |
| Toluene | 30.07% |
| Butyl acetate | 21.685% |
| Ethyl acetate | 9.29% |
| Isopropyl alcohol | 7.74% |
| Stearalkonium hectorite | 1.35% |
| Pigments | 1.00% |
| Citric acid | 0.055.% |

EXAMPLE 9

| | |
|---|---|
| Aminosilicone "KF865" of the Company Shin-Etsu | 0.3% |
| Organofluorinated compound "Nofable Fo 9982" of the Company Nippon Oil | 0.5% |

Drying time (30° C.–50% relative humidity)=14 minutes

EXAMPLE 10

| | |
|---|---|
| Nitrocellulose | 10.84% |
| Toluenesulphonamide-formaldehyde resin | 9.76% |
| Tributyl acetylcitrate | 6.51% |
| Toluene | 30.97% |
| Butyl acetate | 21.685% |
| Ethyl acetate | 9.29% |
| Isopropyl alcohol | 7.74% |
| Stearalkonium hectorite | 1.35% |
| Pigments | 1.00% |
| Citric acid | 0.055% |
| 1-(2'-(F-Hexyl)ethylthio)-3-(2"-ethyl-hexyloxy)-2-propanol | 0.5% |
| Thiosilicone "X22-167B" of the Company Shin-Etsu | 0.3% |

Drying time (30° C.–50% relative humidity)=17 minutes

EXAMPLE 11

| | |
|---|---|
| Nitrocellulose | 10.84% |
| Toluenesulphonamide-formaldehyde resin | 9.76% |
| Tributyl acetylcitrate | 6.51% |
| Toluene | 30.97% |
| Butyl acetate | 21.685% |
| Ethyl acetate | 9.29% |
| Isopropyl alcohol | 7.74% |
| Stearalkonium hectorite | 1.35% |
| Pigments | 1.00% |
| Citric acid | 0.055% |
| 1-(2'- (F-Hexyl)ethylthio)-3-(2"-ethyl-hexyloxy)-2-propanol | 0.5% |
| Thiosilicone "X22-980" of the Company Shin-Etsu | 0.3 |

Drying time (30° C.–50% relative humidity) 16 minutes

EXAMPLE 12: (comparative)

| | |
|---|---|
| Nitrocellulose | 10.9% |
| Toluenesulphonamide-formaldehyde resin | 9.8% |
| Tributyl acetylcitrate | 6.495% |
| Toluene | 31.105% |
| Butyl acetate | 21.8% |
| Ethyl acetate | 9.395% |
| Isopropyl alcohol | 7.8% |
| Stearalkonium hectorite | 1.355% |
| Pigments | 1.00% |
| Citric acid | 0.055% |
| Thiosilicone "X22-980" of the Company Shin-Etsu | 0.3% |

Drying time (30° C.–50% relative humidity)=22 minutes

This example, with respect to Example 11, shows that the absence of the organofluorinated hydrocarbon compound has the effect of increasing the drying time.

EXAMPLE 13

| | |
|---|---|
| Nitrocellulose | 10.8% |
| Toluenesulphonamide-formaldehyde resin | 12.2% |
| Tributyl acetylcitrate | 6.52% |
| Stearalkonium hectorite | 1.23% |
| Ethyl acetate | 40.38% |
| Butyl acetate | 19.3% |
| Isopropyl alcohol | 3.05% |
| Citric acid | 0.05% |
| Pigments | 1.0% |
| 1-(2'- (F-Hexyl)ethylthio-3-(2"-ethyl-hexyloxy)-2-propanol | 0.3% |
| Aminosilicone "KF 865" of the Company Shin-Etsu | 0.5% |

Drying time (30° C.–50% relative humidity)=11 minutes

EXAMPLE 14

| | |
|---|---|
| Nitrocellulose | 9.6% |
| Alkyd resin sold under the name of "Beckosol ODE" by the Company Dai-Nippon | 14.63% |
| Tributyl acetylcitrate | 7.56% |
| Stearalkonium hectorite | 2.43% |
| Ethyl acetate | 31.05% |
| Butyl acetate | 24.35% |
| Isopropyl alcohol | 3.72% |
| Citric acid | 0.75% |
| Pigments | 1.0% |
| 1-(2'-(F-Hexyl)ethylthio)-3-(2'-ethyl hexyloxy)-2-propanol | 0.3% |
| Aminosilicone "KF 865" of the Company Shin-Etsu | 0.5% |

Drying time (30° C.–50% relative humidity)=11.5 minutes.

What is claimed is:

1. A colored or colorless nail varnish comprising, in a nail varnish solvent consisting of a mixture of organic solvents:
   (a) 5 to 20% by weight of a film-forming substance;
   (b) 0.5 to 15% by weight of a resin;
   (c) 2 to 10% by weight of a plasticizer; and
   (d) a mixture of:
      (i) 0.05 to 5% by weight of an aminofunctional silicone having an amine index of between 0.05 and 2.3 or 0.05 to 5% by weight of a thiofunctional silicone having an amount of thiol groups between 0.1 to 15% by weight, said aminofunctional silicone and thiofunctional silicone having a molecular weight between 500 and 100,000; and
      (ii) 0.05% to 5% by weight of an organofluorinated hydrocarbon compound having a fluorine substitution rate of between 0.5 and 95% and a boiling point greater than 30° C.;
   wherein the total weight of (i) and (ii) is less than or equal to 5% by weight based on the total weight of the varnish.

2. A method of applying a nail varnish to nails comprising:
   applying to said nails a composition comprising, in a nail varnish solvent consisting of a mixture of organic solvents:
   (a) 5 to 20% by weight of a film-forming substance;
   (b) 0.5 to 15% by weight of a resin;
   (c) 2 to 10% by weight of a plasticizer; and
   (d) a mixture of:
      (i) 0.05 to 5% by weight of an aminofunctional silicone having an amine index of between 0.05 and 2.3 or 0.05 to 5% by weight of a thiofunctional silicone having an amount of thiol groups between 0.1 to 15% by weight, said aminofunctional silicone and thiofunctional silicone having a molecular weight between 500 and 100,000; and
(ii) 0.05% to 5% by weight of an organofluorinated hydrocarbon compound having a fluorine substitution rate of between 0.5 and 95% and a boiling point greater than 30° C.;

wherein the total weight of (i) and (ii) is less than or equal to 5% by weight based on the total weight of the varnish.

3. The nail varnish according to claim 1, wherein the organofluorinated hydrocarbon compound has a fluorine substitution rate greater than 10% and less than 80%.

4. The nail varnish according to claim 1, wherein the aminosilicone corresponds to the following general formula:

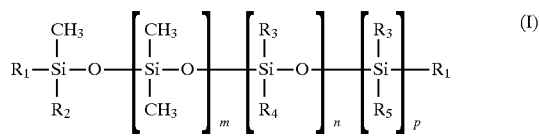

in which:

$R_1$ represents $CH_3$, $OCH_3$, $OCH_2CH_3$ or $-(CH_2)_d-NH_2$ $R_2$ represents $CH_3$, $OCH_3$ or $OCH_2CH_3$, $R_3$ represents $CH_3$, $OCH_3$, $OCH_2CH_3$ or $OSi(CH_3)_3$, $R_4$ represents $CH_3$ or

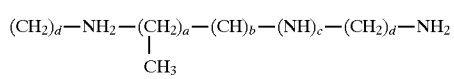

$R_5$ represents $CH_3$, $OCH_3$, $OCH_2CH_3$ or

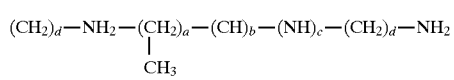

a is 0 to 6
b is 0 to 2
c is 0 or 1
d is 1 to 6 with the proviso that:
(i) when $R_1$ represents the $-(CH_2)_d-NH_2$ radical, $R_4$ represents $CH_3$ and $R_5$ represents $CH_3$, $OCH_3$ or $OCH_2CH_3$,
(ii) when $R_4$ represents $CH_3$, $R_5$ represents:

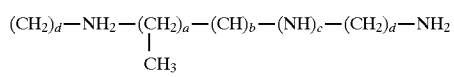

and
(iii) when $R_4$ represents

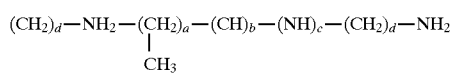

$R_5$ represents $CH_3$, $OCH_3$ or $OCH_2CH_3$,
m is 1 to 1,000
n is 0 to 50 and
p is 0 to 50
n and p being not simultaneously 0,
the molecular weight of the said aminosilicone being between 500 and 100,000.

5. The nail varnish according to claim 1, wherein the thiosilicone is a polydiorganosiloxane containing, in the molecule, at least one unit of formula:

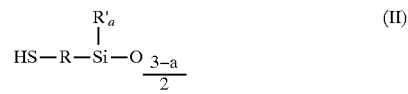

in which:

R denotes a divalent aliphatic radical having from 2 to 26 carbon atoms which is optionally interrupted by an ester functional group and which can carry ethylene oxide or propylene oxide units or their mixture, R' denotes a monovalent hydrocarbon radical having 1 to 6 carbon atoms, an alkoxy radical having 1 to 4 carbon atoms or a trimethylsilyloxy radical, a denotes an integer equal to 0, 1 or 2, the remaining units having the formula:

1)

in which:

R" represents a $C_1-C_{18}$ alkyl, phenyl($C_1-C_6$)alkyl or phenyl group, b is an integer denoting 1, 2 or 3, at least 50% of the R' and R" groups representing a methyl group, and 2) optionally units of formula:

in which

R" is as defined above and n is an integer from 1 to 18.

6. The nail varnish according to claim 5, wherein in the unit of formula (II), the R radical represents $-(CH_2)_n-$, where n is between 3 and 8, or a group of formula:

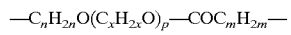

in which:

n represents an integer between 1 and 18, m represents an integer between 1 and 8, x=2 or 3 and when x=3, the $C_3H_6$ radical is branched and p is 0 to 40, and R' represents a $C_1-C_6$ alkyl radical.

7. The nail varnish according to claim 1, wherein the organofluorinated hydrocarbon compound corresponds to the following general formula:

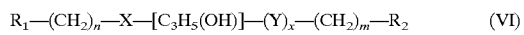

in which:

the divalent radical $C_3H_5(OH)$ represents at least one of the following divalent radicals:

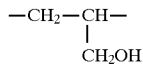(c)

$R_1$ represents a linear or branched $C_4$–$C_{20}$ perfluoroalkyl radical or a mixture of such linear or branched $C_4$–$C_{20}$ perfluoroalkyl radicals, $R_2$ represents $R_1$ or a linear or branched $C_1$–$C_{22}$ alkyl radical or a mixture of such linear or branched $C_1$–$C_{22}$ alkyl radicals or a $C_6$–$C_{10}$ aryl or $C_7$–$C_{15}$ aralkyl radical, with the proviso that:

(i) when $R_2$ is different from $R_1$,

X and Y represent —O—,

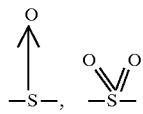

or —S—, X and Y being not simultaneously

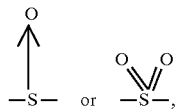

and (ii) when $R_2$ represents $R_1$, X and Y are identical to one another and represent —O— or —S— m and n, identical or different, are between 0 and 4 and x represents 0 or 1.

8. The nail varnish according to claim 1, wherein the organofluorinated compound is selected from the group consisting of:

1-(2'-(F-hexyl)ethylthio)-3-(2"-ethylhexyloxy)-2-propanol, 1-(2'-(F-octyl)ethylthio)-3-(2"-ethylhexyloxy)-2-propanol, 1-(2'-(F-octyl)ethylthio)-3-butyloxy-2-propanol, 1-(2'-(F-octyl)ethylthio)-3-phenoxy-2-propanol, 1-(2'-(F-hexyl)ethylthio)-3-dodecyloxy-2-propanol, 1-(2'-(F-hexyl)ethylthio)-2-decanol, 1-(2'-(F-hexyl)ethylthio)-2-hexanol, 1-(2'-(F-octyl)ethylthio)-2-hexanol, 1-(2'-(F-hexyl)ethyloxy)-3-(2"-ethylhexyloxy)-2-propanol, 1-(2'-(F-hexyl)ethylthio)-3-octylthio-2-propanol, 1-(2'-(F-octyl)ethylthio)-3-octadecylthio-2-propanol, 1,3-bis(2'-(F-hexyl)ethylthio)-2-propanol, and 1,3-bis(2'-(F-octyl)ethylthio)-2-propanol.

9. The nail varnish according to claim 1, wherein the organofluorinated compound corresponds to the following general formula:

$$R_1-CH_2-CH_2-X-CH_2-CH-Z \quad\quad (X)$$
$$\hspace{6em}|$$
$$\hspace{6em}Y$$

in which:

$R_1$ represents a linear or branched $C_4$–$C_{20}$ perfluoroalkyl radical or a mixture of such linear or branched $C_4$–$C_{20}$ perfluoroalkyl radicals, Y represents OH or —CH$_2$OH when Y is OH, Z represents —CH$_3$, —CH$_2$OH, —CH$_2$OCOCH$_3$ or —C$_6$H$_5$, and when Y is —CH$_2$OH Z represents —OCOCH$_3$, and X represents —O—, —S—,

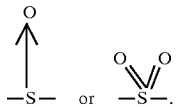

10. The nail varnish according to claim 9, wherein the organofluorinated compound is selected from the group consisting of:

2-(2'-(F-hexyl)ethylthio)-1-phenylethanol, and 2-(2'-(F-hexyl)ethylsulphonyl)-1-phenylethanol.

11. The nail varnish according to claim 1, wherein the organofluorinated compound corresponds to the following general formula:

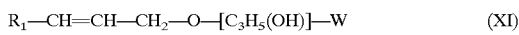

in which:

the divalent radical $C_3H_5$(OH) represents at least one of the following divalent radicals:

$R_1$ represents a linear or branched $C_4$–$C_{20}$ perfluoroalkyl radical or a mixture of such linear or branched $C_4$–$C_{20}$ perfluoroalkyl radicals, W represents —OR, —SR, —COOR, —O—C$_6$H$_5$, ortho- or para-O—C$_6$H$_4$(CH$_3$) or ortho- or para-O—C$_6$H$_4$(OH), R representing a linear or branched $C_1$–$C_{18}$ alkyl radical.

12. The nail varnish according to claim 11, wherein the organofluorinated compound is selected from the group consisting of:

1-(3'-(F-hexyl)-2'-propenoxy)-3-octylthio-2-propanol, 1-(3'-(F-hexyl)-2'-propenoxy)-3-butyloxy-2-propanol, and 1-(3'-(F-octyl)-2'-propenoxy)-3-octadecylthio-2-propanol.

13. Nail varnish according to claim 1, characterized in that the organofluorinated hydrocarbon compound corresponds to the following formula:

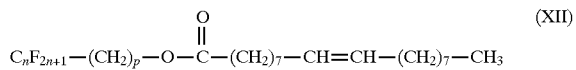

in which:

n is an integer equal to 6 or 8 and p is 1 or 2.

14. The nail varnish according to claim 1, said varnish comprises an organic or inorganic pigment.

15. Nail varnish according to claim 1, wherein the pigment is present at a concentration of between 0.01 and 2% with respect to the total weight of the varnish.

* * * * *